US 12,408,821 B2

(12) United States Patent
Bharos et al.

(10) Patent No.: US 12,408,821 B2
(45) Date of Patent: Sep. 9, 2025

(54) ADAPTABLE DEVICES, SYSTEM, AND METHODS FOR PROVIDING SEALABLE ACCESS TO A WORKING CHANNEL

(71) Applicant: BOSTON SCIENTIFIC MEDICAL DEVICE LIMITED, Galway (IE)

(72) Inventors: Amit Bharos, Jabalpur (IN); Swami Upadhyay, Raipur (IN); Venkata Minnikanti, Vetapalem (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 124 days.

(21) Appl. No.: 17/554,744

(22) Filed: Dec. 17, 2021

(65) Prior Publication Data

US 2022/0211254 A1 Jul. 7, 2022

Related U.S. Application Data

(60) Provisional application No. 63/133,903, filed on Jan. 5, 2021.

(51) Int. Cl.
*A61B 1/00* (2006.01)

(52) U.S. Cl.
CPC ...... *A61B 1/00121* (2013.01); *A61B 1/00137* (2013.01); *A61B 1/00128* (2013.01)

(58) Field of Classification Search
CPC ............ A61B 1/00121; A61B 1/00137; A61B 1/00128

(Continued)

(56) References Cited

U.S. PATENT DOCUMENTS 4,414,608 A * 11/1983 Furihata ............. A61B 1/00124
396/17
4,920,953 A * 5/1990 McGown ........... A61B 1/00137
600/154

(Continued)

FOREIGN PATENT DOCUMENTS

JP 2012525219 A 10/2012
JP 2017189458 A 10/2017

(Continued)

OTHER PUBLICATIONS

Exalt Model D Single-use Duodenoscope, Boston Scientific, 3 pgs., (2020).

(Continued)

*Primary Examiner* — John P Leubecker
(74) *Attorney, Agent, or Firm* — Seager, Tufte & Wickhem, LLP

(57) ABSTRACT

An adapter for allowing a cap assembly to fit securely on two or more medical device ports with different sizes, shapes, and/or dimensions. The cap assembly has a housing with an interior configuration corresponding with an exterior configuration of a first port and surrounding port region of a medical device. An adapter having an exterior configuration corresponding with the housing interior configuration, and an interior configuration corresponding with the second port and port region may be fitted within the housing. Alternatively, an adapter having a first configuration may be provided in the housing to configure the housing interior to correspond with the exterior configuration of the first port. The adapter may be shiftable into a second configuration with an interior corresponding with the exterior configuration of the second port. The first and second configurations of the housing interiors adapt the housing to fit securely on the corresponding port.

18 Claims, 11 Drawing Sheets

(58) Field of Classification Search
USPC .......................................................... 600/154
See application file for complete search history.

(56) References Cited

U.S. PATENT DOCUMENTS

| | | | | |
|---|---|---|---|---|
| 5,514,098 A * | 5/1996 | Pfoslgraf | ..........  | A61M 39/0606 604/167.04 |
| 5,863,286 A * | 1/1999 | Yabe | .................... | A61B 1/0051 600/122 |
| 6,117,070 A * | 9/2000 | Akiba | ................ | A61B 1/00137 600/154 |
| 7,025,721 B2 * | 4/2006 | Cohen | ................ | A61B 1/00137 600/153 |
| 7,927,271 B2 * | 4/2011 | Dimitriou | .......... | A61B 1/00128 600/153 |
| 10,238,272 B2 * | 3/2019 | Simmons | ........... | A61B 1/00128 |
| 10,709,315 B2 * | 7/2020 | Gavalis | .............. | A61B 1/00133 |
| 2005/0090835 A1 * | 4/2005 | Deal | .................. | A61B 1/00137 606/1 |
| 2005/0171402 A1 | 8/2005 | Cohen et al. | | |
| 2007/0114777 A1 * | 5/2007 | Gray | ....................... | B60R 22/24 280/808 |
| 2007/0276180 A1 * | 11/2007 | Greenburg | ............. | A61B 90/57 600/106 |
| 2009/0088600 A1 * | 4/2009 | Meloul | ................ | A61B 1/2676 600/154 |
| 2010/0280311 A1 | 11/2010 | McGrath | | |
| 2011/0099773 A1 * | 5/2011 | Golden | .............. | A61B 1/00128 24/457 |
| 2014/0265313 A1 * | 9/2014 | Durr | .................... | A61B 1/0014 285/305 |
| 2015/0057537 A1 * | 2/2015 | Dillon | .................. | A61B 1/0014 600/113 |
| 2018/0014717 A1 | 1/2018 | Benn et al. | | |
| 2018/0042603 A1 * | 2/2018 | Mitelberg | .......... | A61B 1/00101 |
| 2018/0279859 A1 | 10/2018 | Eveland et al. | | |
| 2019/0046016 A1 * | 2/2019 | Rajarathnam | ...... | A61B 1/00094 |
| 2020/0138272 A1 | 5/2020 | Neelamegam et al. | | |
| 2020/0138273 A1 | 5/2020 | Neelamegam et al. | | |
| 2020/0138276 A1 | 5/2020 | Aneja et al. | | |
| 2020/0138277 A1 | 5/2020 | Neelamegam et al. | | |

FOREIGN PATENT DOCUMENTS

| | | | | |
|---|---|---|---|---|
| WO | WO-2016189533 A1 * | 12/2016 | ......... | A61B 1/00089 |
| WO | 2020089866 A1 | 5/2020 | | |

OTHER PUBLICATIONS

International Search Report and Written Opinion dated Feb. 25, 2022 for International Application No. PCT/IB2021/061981.

* cited by examiner ions for the various aspects and features of the disclo-

ADAPTABLE DEVICES, SYSTEM, AND METHODS FOR PROVIDING SEALABLE ACCESS TO A WORKING CHANNEL

PRIORITY

The present application is a non-provisional of, and claims the benefit of priority under 35 U.S.C. § 119 to U.S. Provisional Application Ser. No. 63/133,903, filed Jan. 5, 2021, the disclosure of which is hereby incorporated herein by reference in its entirety for all purposes.

FIELD

The present disclosure relates generally to the field of medical devices and components for use with endoscopes. In particular, the present disclosure relates to cap assemblies, including housings and caps within the housings, for coupling with or mounting on access ports of endoscopes.

BACKGROUND

Endoscopes are used during a variety medical procedures. The proximal end of the endoscope generally remains in the control of the physician's hands for navigation, irrigation, visualization, insufflation, device management, etc. One or more ports are provided on the proximal end (e.g., handle) of the endoscope. During various medical procedures, various medical devices, tools, and instruments (e.g., for both diagnostic and therapeutic purposes) are inserted through the one or more ports to be navigated through the endoscope to the procedure site. The devices, tools, and instruments are removed via the port, and sometimes exchanged with other devices, tools, or instruments Caps (also known as biopsy caps) have been introduced to fit over the endoscope ports and to provide access to the endoscopic device passage and exchange, such as to help maintain insufflation, to provide better sealing in wide usage conditions, etc. The caps are often associated (e.g., fit within) a housing configured to couple the cap to the endoscope. One drawback is that such caps and/or housings generally are shaped, dimensioned, and configured to be mounted on a particular shape and configuration of an endoscope port with a generally set dimension. As ports may vary from endoscope to endoscope, the biopsy cap may provide the desired sealing performance and device stability when used with the port for which the cap was designed, but may not perform as well with ports having different shapes, sizes, dimensions, and/or configurations.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, a cap assembly configured to be coupled to a port of a medical device is provided with a housing having an upper portion configured to house a cap, and a lower portion with an interior having a configuration corresponding with an exterior configuration of a first port of a medical device, and an adapter securely fitted within the interior of the housing and having an interior configuration corresponding with a second port of a medical device.

In some embodiments, the adapter has an exterior configuration corresponding to the housing lower portion interior configuration. In some embodiments, the exterior of the adapter engages the interior of the lower portion of the housing with a surface-to-surface contact to ensure a secure engagement therebetween. In some embodiments, the housing lower portion interior includes one or more ribs or grooves and the adapter exterior includes one or more grooves or ribs mating with the housing ribs or grooves.

In some embodiments, the housing includes at least one stabilizing shoulder extending inwardly from the interior of the lower portion of the housing. In some embodiments, the cap assembly further includes a cap positioned within the housing upper portion; and the cap includes a base seated and stabilized on the stabilizing shoulder. In some embodiments, the adapter further includes one or more hooks fitted between an upper surface of the stabilizing shoulder and a lower surface of the base. In some embodiments, the adapter further includes one or more hooks fitted between an upper surface of the stabilizing shoulder. In some embodiments, the housing includes a pair of locking tabs extending inwardly from opposite sides of the interior of the lower portion of the housing, the locking tabs being formed of a flexible, resilient, creep resistant, dimensionally stable material and configured to securely engage the first port or the second port. In some embodiments, the adapter further includes at least one projection positioned to engage one of the locking tabs to at least inhibit lateral shifting of the locking tabs with respect to the second port.

In some aspects of the present disclosure, the adapter is shiftable between a first configuration in which the adapter interior configuration is the interior configuration of the housing lower portion corresponding with an exterior configuration of a first port, and a second configuration in which the adapter interior configuration corresponds with an exterior configuration of a second port of a medical device. In some embodiments, the adapter includes at least one actuator accessible from an exterior of the housing. In some embodiments, the adapter includes a movable component and a gripper component; the actuator is provided on the movable component; the gripper component includes gripper portions with gripper surfaces shaped to correspond to the outer surfaces of a neck of either the first port or the second port; and the actuator is movable with respect to the housing to move the movable component to move the gripping components between a first position at a first distance away from each other and a second position at a second distance away from each other, the first distance being greater than the second distance, to shift the configuration of the adapter between the first configuration and the second configuration. In some embodiments, the movable component and the gripper component have corresponding cam surfaces.

In some embodiments, the first port is on a first endoscope and the second port is on a second endoscope, the adapter configuring the housing for coupling to two different endoscopes.

In one aspect of the present disclosure, an adapter is configured to fit within the interior of a lower portion of a housing of a cap assembly, the housing lower portion interior having a configuration corresponding with an exterior configuration of a first port of a medical device and a first port region of the medical device surrounding the first port to securely engage the cap assembly with the first port without the adapter fitted therein, the adapter having: an exterior configuration corresponding with the configuration of the interior of the housing lower portion to establish a surface-to-surface contact with the interior of the housing lower portion to securely fit within the housing lower portion; and an interior configuration corresponding with the exterior configuration of a second port of a medical device and a second port region of the medical device surrounding the second port to securely engage the cap assembly, with the adapter fitter therein, with the second port, the second port region being narrower than the first port region.

In some embodiments, the adapter further includes one or more hooks configured to fit between an upper surface of a stabilizing shoulder in the cap assembly housing and a lower surface of a base of a cap seated within an upper portion of the cap assembly housing and on the stabilizing shoulder.

In another aspect of the present disclosure, an adapter is configured to fit within the interior of a lower portion of a housing of a cap assembly to shift an interior configuration of the housing lower portion between a first configuration for securely engaging a first port of a medical device and a second configuration for securely engaging a second port of a medical device, the adapter including: a gripper component including gripper portions with gripper surfaces shaped to securely engage the neck of a port of a medical device; and at least one movable component; where the movable component is movable with respect to the gripper component to move at least one of the gripper portions with respect to another gripper portion.

In some embodiments, at least one movable component is shifted via an actuator accessible through a window in the housing lower portion. In some embodiments, the at least one movable component has a cam actuator with a cam surface; the at least one gripper portion has a cam surface corresponding with the cam actuator cam surface; and movement of the movable component with respect to the gripper component causes the cam actuator cam surface and the at least one gripper portion cam surface to slide with respect to each other to cause the at least one gripper portion to move with respect to another gripper portion.

These and other features and advantages of the present disclosure, will be readily apparent from the following detailed description, the scope of the claimed invention being set out in the appended claims. While the following disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the relative dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
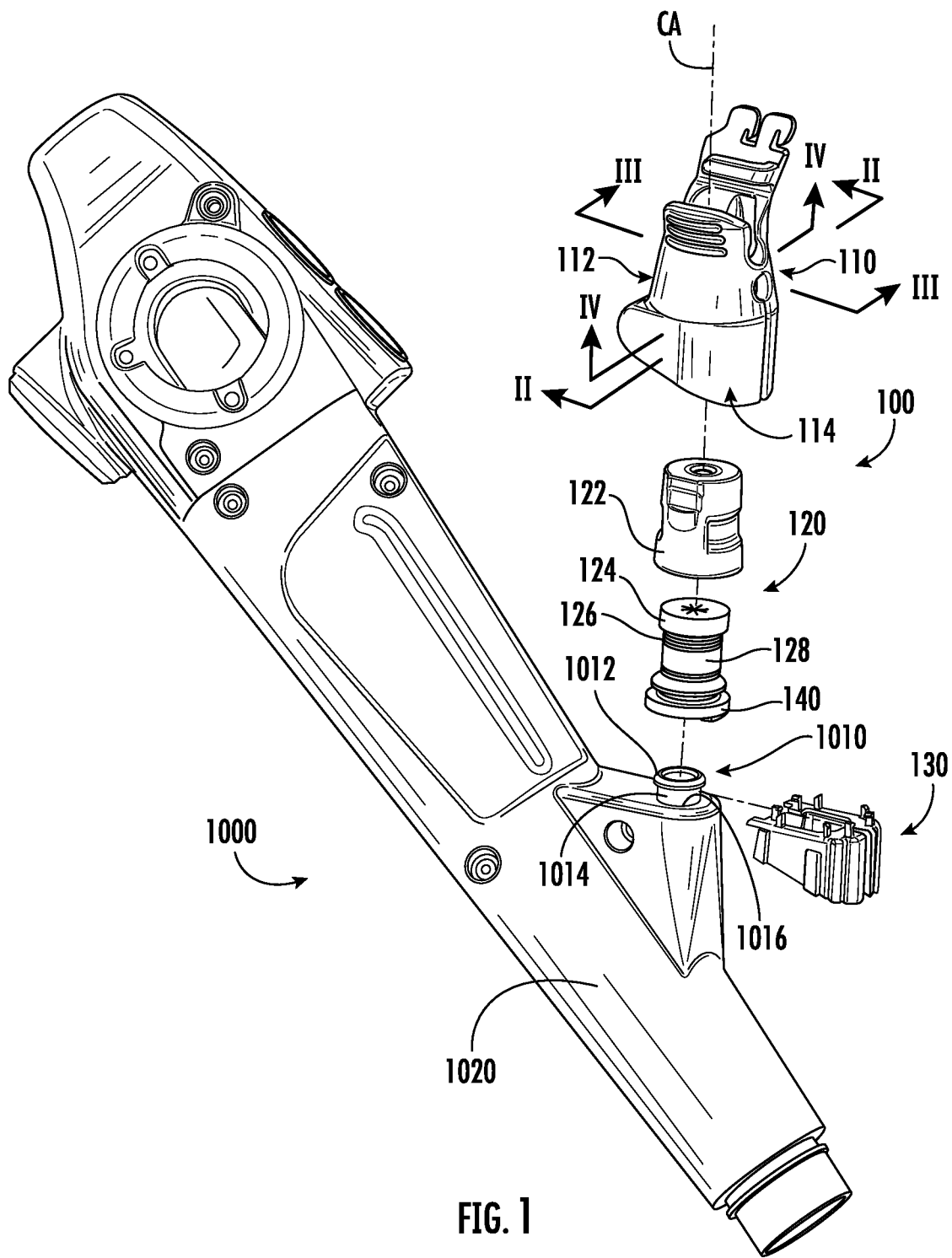
FIG. 1 is an exploded perspective view of a cap assembly in accordance with aspects of the present disclosure shown positioned with respect to a port of a medical device handle.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician or endoscopist, etc., such terms being used interchangeably herein without intent to limit, and including automated controller systems or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, a cavity, or a bore.

In accordance with various principles of the present disclosure, a cap assembly, including a cap and a cap housing, is configured to securely fit on more than one port of a medical device. More particularly, the cap housing may be configured to securely fit on more than one port of a medical device to couple (such term and conjugations thereof being used interchangeably herein with mount, secure, fit, and the like, without intent to limit) the cap with respect to the port. The medical device may be an endoscope (including, without intent to limit, gastroscopes, bronchoscopes, colonoscopes, ureteroscopes, and the like), the port thereof allowing access to the endoscope's working channel by one or more medical tools, instruments, or devices (such terms may be used interchangeably herein without intent to limit). The port may be provided on a handle of the endoscope which may provide various navigational functions to the medical professional. Although various endoscopes are sterilizable, infection prevention controls in the clinical setting create a demand for single-use scopes, which mitigate the risk of patient infection and associated adverse events without the need for sterilization equipment and processes. The various ports on an endoscope or various ports of different endoscopes may have different dimensions, such as height (e.g., between the bottom of a flange typically provided around the port opening and the surrounding area of the medical device, such as a shoulder or other handle surface surrounding the port) and/or diameter (e.g., of the neck of the port). The cap assembly often is configured to securely engage a port region of the medical device (a portion or surface of the medical device, e.g., endoscope handle, surrounding or adjacent to the port). Variations in materials used to make medical devices (e.g., materials used for reusable medical device may be different from materials used for single-use or disposable medical devices) may lead to different sizes, shapes, configurations, and/or dimensions of the port (or portions thereof) and/or port region.

A port cap provides a secure (e.g., tight) fluid/air barrier to the working channel of the medical device that may help control insufflation and/or fluid (e.g., bile) egress therefrom without undesired leaks or seepage or spills or the like from the port. The port cap (referenced herein as a "cap" for the sake of convenience and without intent to limit) is generally provided in a cap housing which couples the cap to the port. The cap may include various components (e.g., sealing components) to prevent the leakage of body fluids and/or air.

The housing holds the cap in place to ensure proper functioning of the cap. In some embodiments, the cap housing includes a first portion with an interior configuration which is sized, shaped, configured, and dimensioned to be secured over a first port of a medical device (to couple a cap thereto), and a second portion in which the cap is positioned. The first portion of the cap housing may be referenced herein as a lower portion, and the second portion of the cap housing may be referenced herein as an upper portion for the sake of convenience and without intent to limit. The housing optionally includes instrument-engaging structures configured to engage and to hold in place a medical instrument (e.g., a guidewire, catheter, endoscopic device, and/or the like) with respect to the endoscope.

The cap assembly (and various components thereof) may have an opening (such term being used interchangeably herein with aperture, channel, lumen, hole, bore without intent to limit, such feature not being limited a circular cross-section) therethrough in fluid communication with the working channel of the port and/or medical device. The diameter of the opening (or at least the opening through one or more components of the cap assembly) may be smaller than the diameter of the working channel, such as to form a transition to a size closer to that of a device to be extended through the working channel.

In view of the above, the cap and/or cap housing and/or cap assembly helps prevent undesired leaks, seepage, spills, etc. from the port which may result in contact of biological fluids (or treatment fluids) with the hands of the user holding the endoscope and/or other and/or other individuals in the vicinity of the medical device and/or the floor. Secure engagement of the cap assembly, particularly the housing and cap, minimize or prevent such undesired occurrences.

It will be appreciated that reference is made herein to one or more of the cap, cap housing, or cap assembly in general, for the sake of convenience and without intent to limit unless otherwise indicated.

Generally, a lower portion of a cap housing has an interior configuration corresponding to the exterior configuration of a first port of a medical device. The interior configuration of the lower portion of the cap housing preferably is shaped, sized, and dimensioned to securely engage the exterior of the first port, and optionally also the first port region, to couple the cap securely and stably to the first port. Such configurations which facilitate secure coupling may be described herein as "corresponding" configurations which match or closely match or conform or otherwise mate with each other.

It will be appreciated that reference to a port is generally intended to include reference to the associated or corresponding port region as well, unless explicitly excluded.

In accordance with various principles of the present disclosure, an adapter is provided within the interior of a portion of the cap housing (generally referenced herein as a lower portion for the sake of convenience and without intent to limit) to modify the interior configuration of the cap housing to correspond with the exterior configuration of a second port of a medical device having a different size, shape, configuration, and/or one or more dimension(s) different from the first port. The adapter may have an exterior configuration corresponding with the interior configuration of the portion of the cap housing to fit securely therein. Alternatively or additionally, the adapter may include various locking or engaging structures (e.g., tabs, ribs, shoulders, etc.) configured to engage with the cap housing to hold the adapter securely in place with respect to the cap housing. The adapter may form or otherwise contribute to the interior configuration of the cap housing to correspond to a first port of a medical device. Alternatively, the interior configuration of the cap housing may correspond to the first port of the medical device when the adapter is not positioned therein.

In accordance with one aspect of the present disclosure, the adapter is in the form of an insert fitted within the interior of a cap housing, such as the lower portion of the cap housing, to engage with the interior surface of the lower portion of the cap housing. In some embodiments, the adapter exterior and cap housing interior surface engage via surface-to-surface (in contrast with point-to-point) contact. More particularly, the adapter is sized, shaped, configured, and dimensioned such that, when inserted into a portion of the cap housing, a majority of the exterior surface of the adapter contacts the interior surface of the lower portion of the cap housing. In some embodiments, at least the exterior of the side walls of the adapter are sized, shaped, configured, and dimensioned to substantially match (e.g., substantially be a three-dimensional mirror image of) the interior of the portion the cap housing in which the adapter is to be positioned, such as the side walls of the lower portion of the cap housing. The side walls of the lower portion of the cap housing may be considered a skirt surrounding the medical device port and port region and optionally also additional portions of the medical device (e.g., handle thereof). The surface-to-surface contact between the exterior surface of the adapter and the interior surface of the lower portion of the cap housing inhibits or prevents relative movement therebetween. Optionally, further engagement structures may be provided to engage with additional interior structures within the cap housing. Such engagement structures may also interact with the cap (seated within the cap housing, such as in the upper portion of the cap housing) to secure the adapter in place within the cap housing. It will be appreciated that a greater interference may cause improper assembly, and a greater clearance may result in a less stable design. More specifically, greater interference leads to the improper fit between the cap or cap housing and the scope on which it is mounted, as the locking elements will not engage or lock properly under the biopsy port flange. Greater clearances allow the cap or cap housing to become unstable over the scope or may not provide sufficient connection to the biopsy port flange and thus not function as intended. Accordingly, the adapter is designed to have minor or slight interference, such as approximately 0.005" (0.127 mm), and low clearance, such as approximately 0.010" (0.254 mm), allowing a total range of approximately 0.015" (0.381 mm).

In accordance with another aspect of the present disclosure, an adapter is provided within a cap housing (e.g., a lower portion of the cap housing) and is shiftable between one or more configurations. In a first configuration, the adapter is sized, shaped, configured, and dimensioned to securely engage with a first port of a medical device to couple the cap housing securely thereto. Such first configuration may be considered to be the first configuration of the interior of the cap housing in which the adapter is positioned. In the second configuration, the adapter is sized, shaped, configured, and dimensioned to securely engage with a second port of a medical device to couple the cap housing securely thereto. In some embodiments, the adapter includes at least first and second locking features, such as cam mechanisms, movable with respect to each other to shift the interior of the cam housing between at least a first configuration and a second configuration.

When securely engaged with a port, the cap housing and/or adapter ensures the desired sealing and secure mounting of the cap with respect to two or more different ports of a medical device. The ports may be on the same or different medical devices. In some embodiments, at least one of the configurations of the adapter allows mounting of the cap assembly with respect to a port of a medical instrument independent of the height of the port.

Various embodiments of a cap assembly for coupling with a port of a medical device, and associated components thereof, will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

In the following description and accompanying drawings, it will be appreciated that elements or components similar among the various illustrated embodiments are generally designated with similar reference numbers increased by 100, and redundant description is omitted. Common features are identified by common reference elements and, for the sake of brevity, the descriptions of the common features are generally not repeated. For purposes of clarity, not all components having the same reference number are numbered.

Turning now to the drawings, and with reference to FIG. 1, a cap assembly 100 formed in accordance with various principles of the present disclosure is illustrated exploded along its central axis CA and positioned with respect to a medical device 1000. It will be appreciated that although reference may be made to a "central" axis, such reference is intended to include an axis generally extending along (e.g., parallel to or within a minimal angle with respect to) the central axis CA. More particularly, in the illustrated example, the cap assembly 100 is shown positioned adjacent a first port 1010 on a handle 1020 of a medical device 1000. The cap assembly 100 includes a cap housing 110, a cap 120 configured to fit within an upper portion 112 of the cap housing 110, and an adapter 130 configured to fit within a lower portion 114 of the cap housing 110. The lower portion 114 of the cap housing 110 is configured to engage a portion or region of the medical device 1000 such as surrounding a port 1010. The components of the cap assembly 100 are illustrated in cross-section along line II-II in FIG. 2 and along line III-III in FIG. 3 in an assembled configuration.

Figure 2:
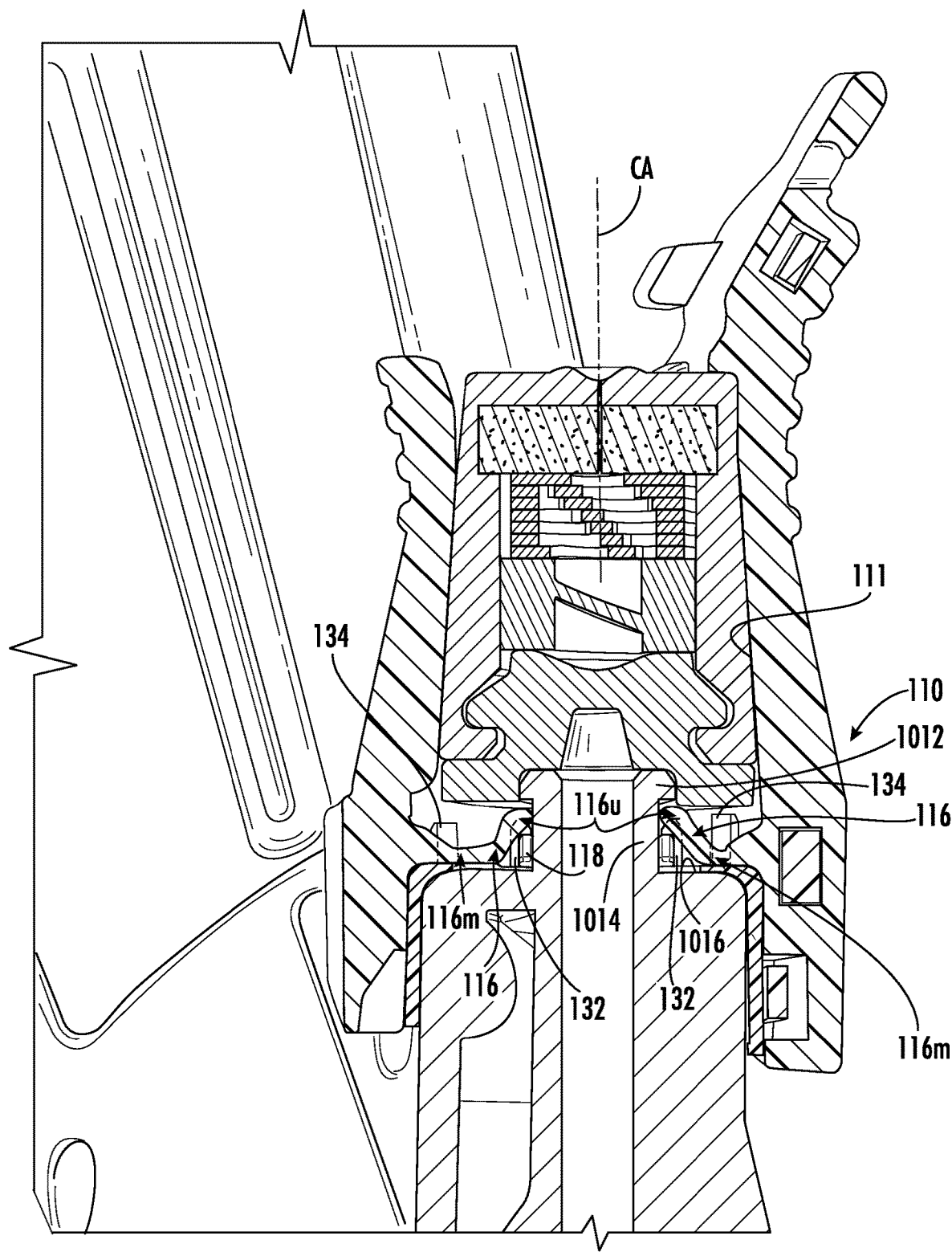
FIG. 2 is a cross-sectional view along line II-II of FIG. 1 of a cap assembly as in FIG. 1 but in an assembled configuration on a medical device port.
Figure 4:
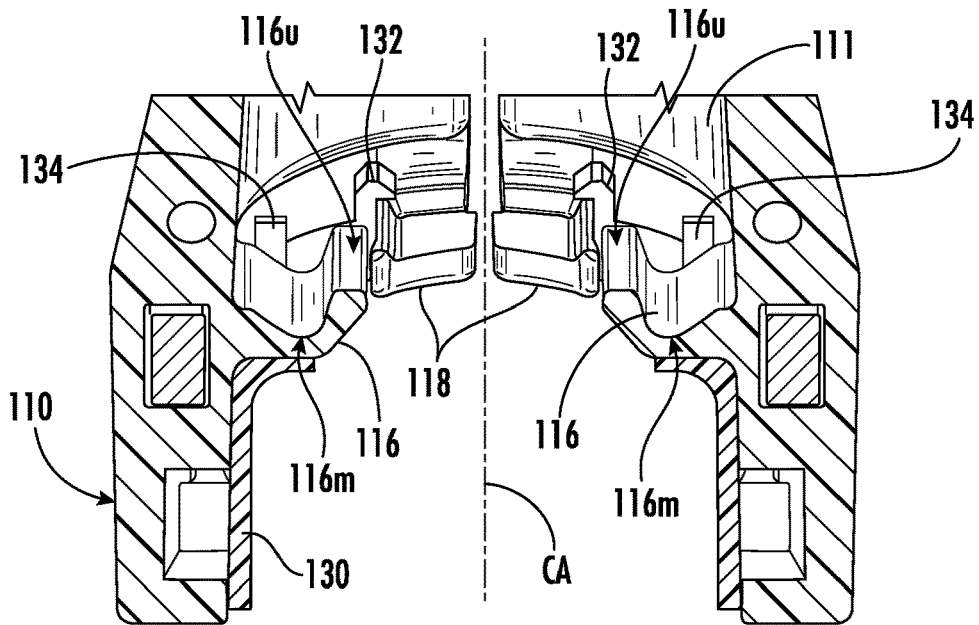
FIG. 4 is a cross-sectional and perspective view along line IV-IV of FIG. 1 of a cap assembly as in FIG. 1 but in an assembled configuration on a medical device port.
Figure 5:
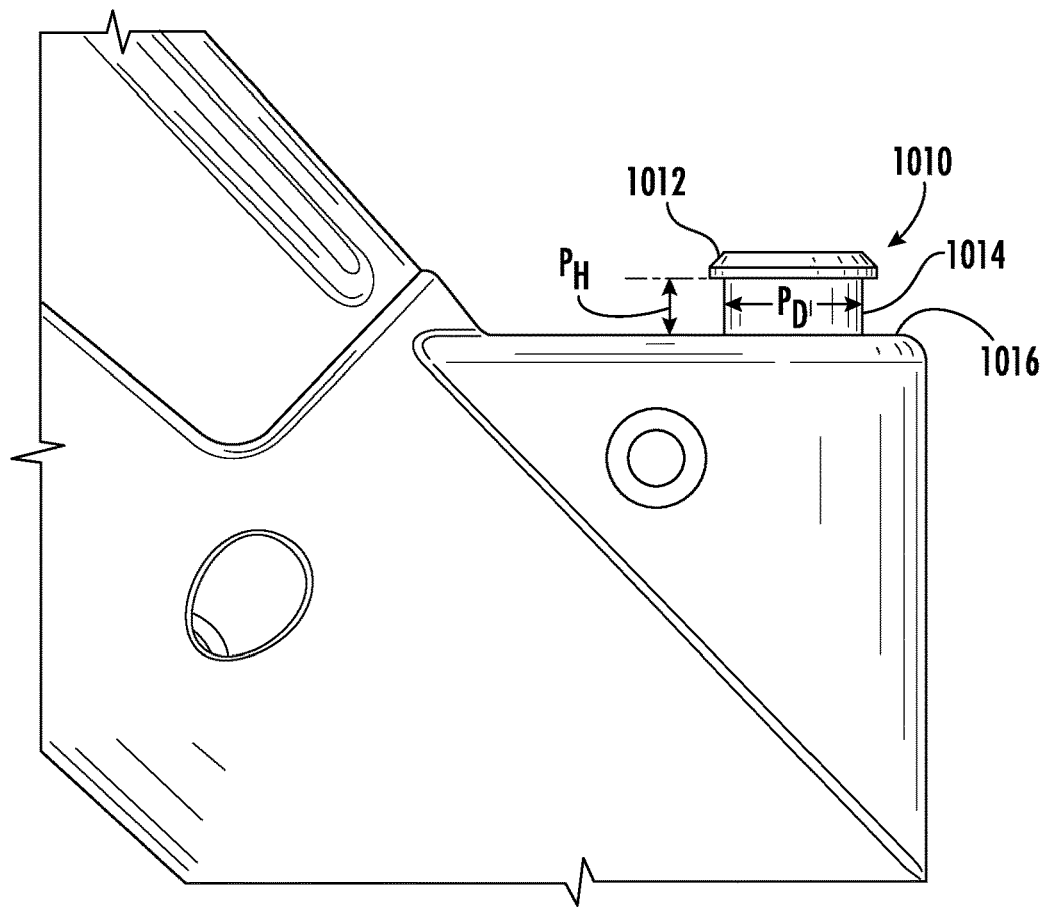
FIG. 5 is an isolated elevational view of an example of a port of a medical device to which a cap assembly formed in accordance with principles of the present disclosure may be mounted.

As may be appreciated with reference to FIG. 2 and FIG. 4, the cap housing 110 includes one or more locking tabs 116 extending radially inwardly from the interior 111 of the cap housing 110 towards the central axis CA of the cap assembly 100. The term "tab", as used herein, is to be understood as not limiting to a particular shape or configuration and may be alternately referenced herein as finger, flange, projection, shoulder, element, member, or the like, without intent to limit. As assembled on the port 1010 (shown in an isolated view in FIG. 5) of the medical device 1000, the locking tabs 116 fit between a lower side or surface of a flange 1012 at the top of the port 1010, around (e.g., on different sides of, such as opposite sides of) the neck 1014 of the port 1010, and above a port region 1016 around the port 1010, as illustrated in FIG. 2. The locking tabs 116 are configured to engage the port 1010 to secure the cap housing 110 and thus the cap 120 with respect to the port 1010. In the illustrated embodiment, the locking tabs 116 are bent, such as in an upward direction (e.g., in a "V" configuration), such that a middle section 116m of the locking tabs 116 rests on the port region 1016 and the upper ends 116u contact the lower side of the flange 1012. It will be appreciated that alternate configurations are within the scope and spirit of the present disclosure. Because exterior dimensions of medical device ports such as the port height $P_H$ and the port diameter $P_D$ (FIG. 5) may vary from port to port and from device to device, the locking tabs 116 preferably are formed of a material which is sufficiently flexible and resilient, yet resistant to creep and with sufficient dimensional stability (materials with appropriately selected tensile modulus, flexure modulus, and/or tensile strain at the yield point) to securely engage the cap housing 110 and thus the cap 120 therein with respect to the port 1010. In some embodiments, the locking tabs 116 fit against the port 1010 with an interference fit. The locking tabs 116 (and optionally also the cap housing 110) may be formed of any of a variety of suitable biocompatible materials with properties as described above with respect to the locking tabs 116, such as metals, metal alloys, polymers, metal-polymer composites, ceramics, combinations thereof, and the like., or other materials such as disclosed in U.S. Patent Application Publication 2020/0138272, published May 7, 2020, and titled "Devices, Systems, And Methods For A Biopsy Cap And Housing"; U.S. Patent Application Publication 2020/0138274, published May 7, 2020, and titled "Attachments For Endoscopes"; or U.S. Patent Application Publication 2020/0138419, published May 7, 2020, and titled "Biopsy Cap And Biopsy Cap Housing", which applications are incorporated herein in their entireties for all purposes.

Figure 3:
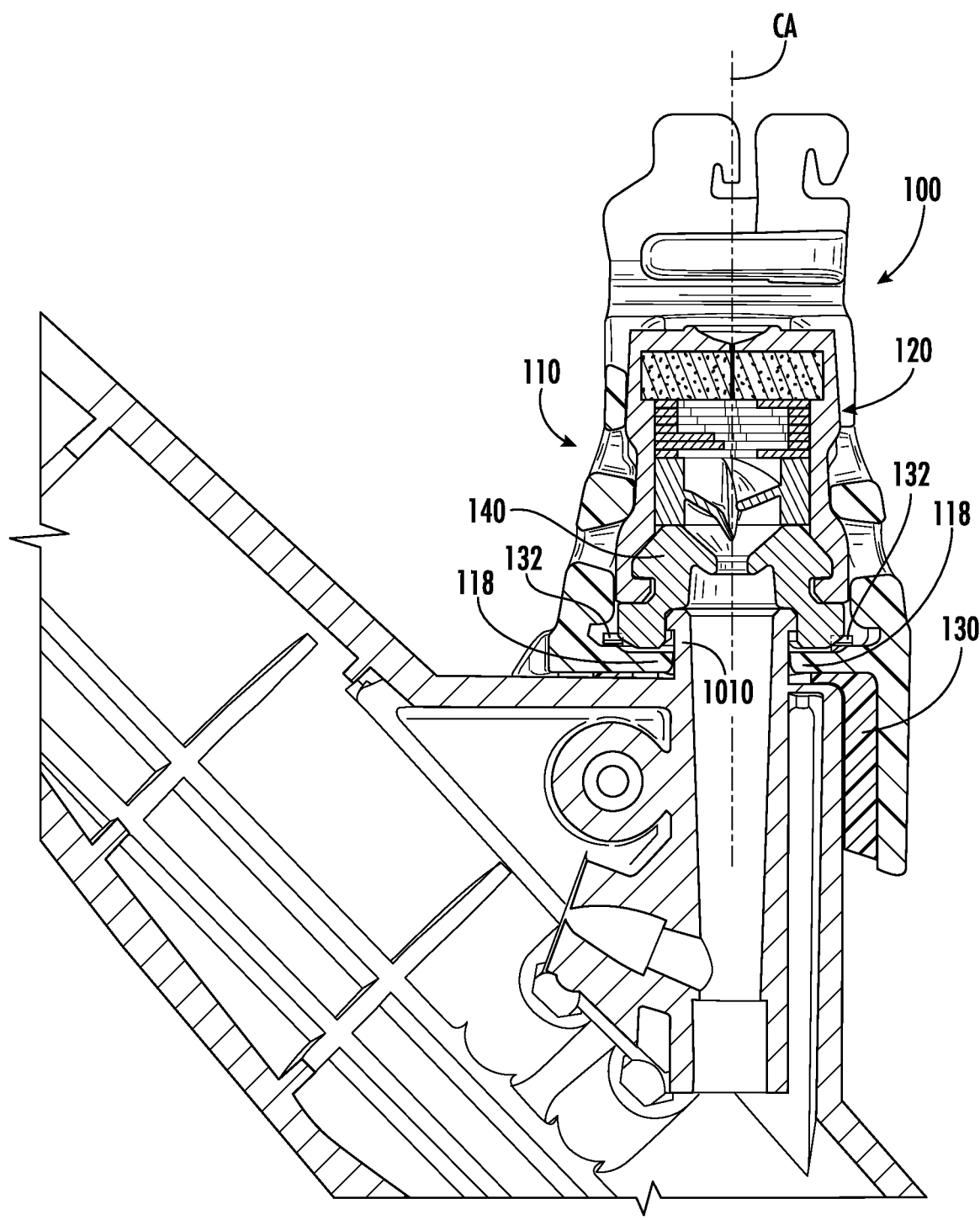
FIG. 3 is a cross-sectional view along line III-III of FIG. 1 of a cap assembly as in FIG. 1 but in an assembled configuration on a medical device port.
Figure 6:
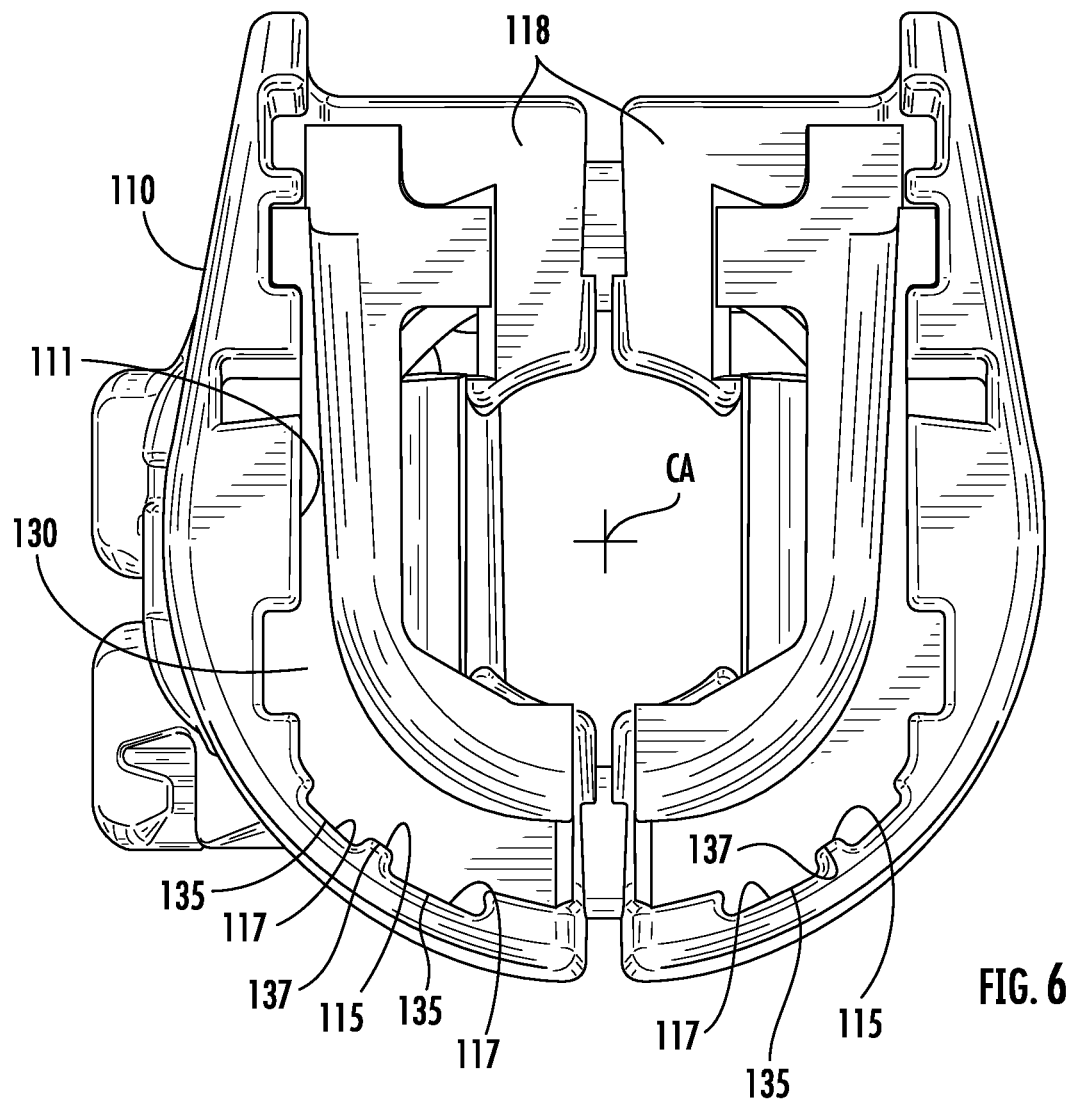
FIG. 6 is a bottom elevational view of a cap housing and adaptor formed in accordance with principles of the present disclosure.

As may be appreciated with reference to FIG. 3, FIG. 4, and FIG. 6, the cap housing 110 may also include one or more stabilizing tabs 118 extending radially inwardly from the interior 111 of the lower portion 114 of the cap housing 110 towards the central axis CA of the cap assembly 100. The stabilizing tabs 118 may be configured to assist with stabilizing the position (lateral and/or axial) of the cap assembly 100 with respect to the port 1010. The stabilizing tabs 118 may also be configured to assist with stabilizing the cap 120 with respect to the cap housing 110 and/or with respect to a port 1010 to which the cap assembly 100 is coupled.

The cap 120 may include a variety of components which contribute to the sealing function of the cap assembly 100. In the example of an embodiment illustrated in FIG. 1, the cap 120 includes an outer shell 122, a foam section 124, a brush section 126, a disk shutter section 128 (optionally having a plurality of fins), and a base 140. The various inner components of the cap 120 (foam section 124, brush section 126, disk shutter section 128, and/or other components) are not critical to the concepts of the present disclosure and thus not described in detail herein. Reference is made to the above-referenced patent applications which have been incorporated herein by reference, as well as to U.S. Patent Application Publication 2019/0046016, published Feb. 14, 2019, and titled "Biopsy Cap For Use With Endoscope"; U.S. Patent Application Publication 2020/0138273, published May 7, 2020, and titled "Internal Seal For Biopsy Cap"; U.S. Patent Application Publication 2020/0138276, published May 7, 2020, and titled "Devices, Systems, And Methods For Providing Sealable Access To A Working Channel"; U.S. Patent Application Publication 2020/0138277, published May 7, 2002, and titled "Devices, Systems, And Methods For Providing Sealable Access To A Working Channel" for details of examples of components of the cap 120, each of such patent applications being incorporated by reference herein in their entireties for all purposes. The base 140 preferably is formed of a suitable biocompatible material which may seal against and around the port 1010 of the medical device 1000. Examples of suitable materials (such as for sealing) include, without limitation, silicone materials such as a liquid silicone rubber (LSR) such as ELASTOSIL© sold by Wacker, and may have a Shore A Hardness of 40 or 50. Alternative materials include Wacker SILPURAN®-640050-AB, Wacker ELASTOSIL® LR 3043/50 A/B, NuSil® SIL 5950, NuSil® MED-4950, Dow Q7-7850, Dow Q7 4850, or Dow C6-750. The base 140 may rest on an upper side of the stabilizing tabs 118, such that the stabilizing tabs 118 stabilize the cap 120 with respect to the port 1010.

The interior 111 of the lower portion 114 of the cap housing 110 may include one or more ribs 115 and/or grooves 117, as may be appreciated with reference to FIG. 6. The ribs 115 and/or grooves 117 may be configured and arranged to form or otherwise define a surface along the interior of the cap housing 110 that allows the lower portion 114 of the cap housing 110 to "grip" onto and/or otherwise frictionally engage the medical device 1000 (e.g., around the port 1010) to assist in securing the cap assembly 100 to the medical device 1000.

As noted above, the exterior dimensions of medical device ports, such as the port height $P_H$ and port diameter $P_D$ (indicated in FIG. 5), may vary from port to port and/or from device to device. As such, the interior 111 of the cap housing 110 may be sized, shaped, configured, and dimensioned to securely engage with a first port, but not necessarily with a second port having different exterior dimensions.

Figure 7:
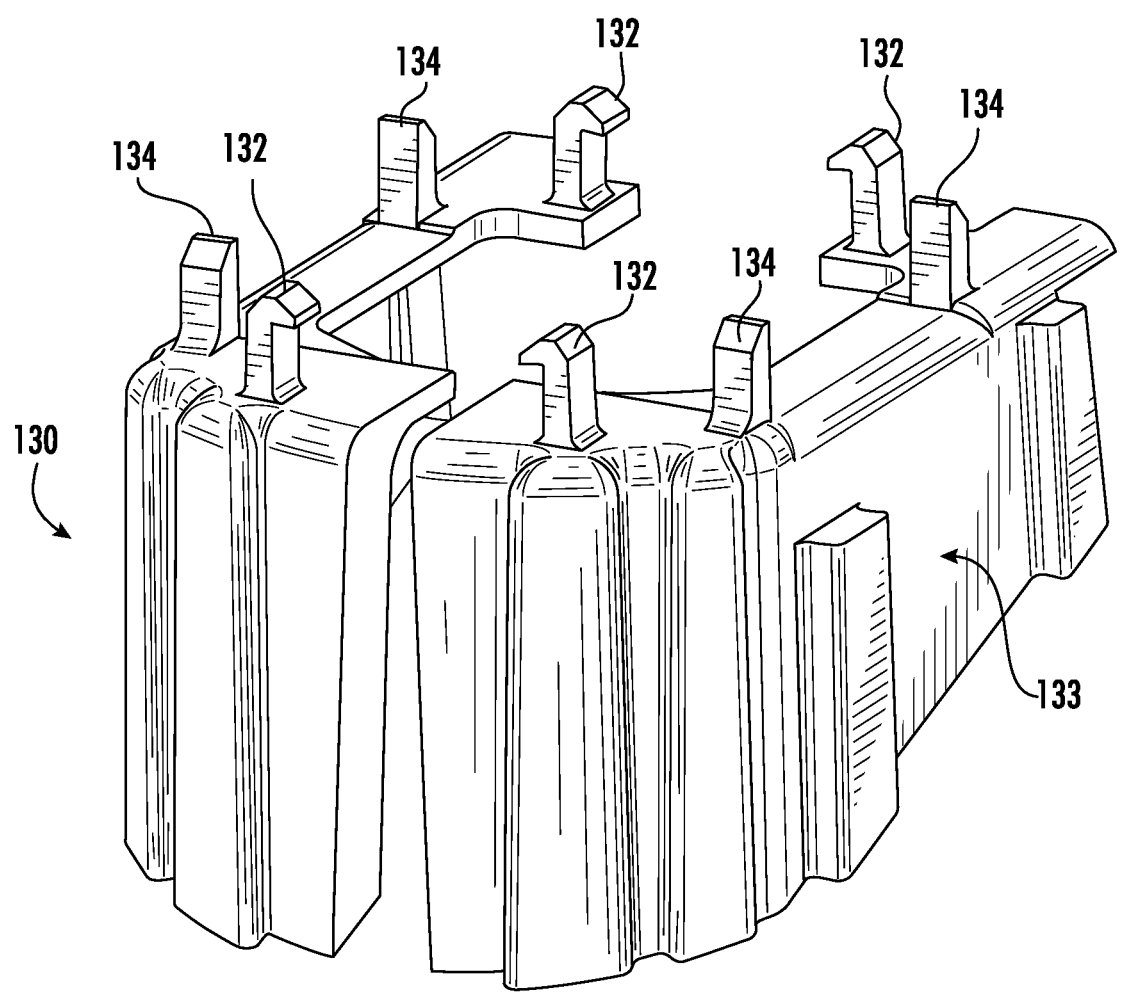
FIG. 7 is a top perspective view of an adaptor formed in accordance with principles of the present disclosure.

In accordance with various principles of the present disclosure, an adapter 130, such as illustrated in FIG. 7, is provided to fit within the lower portion 114 of the cap housing 110 to adapt the cap housing 110 to securely fit on a second port and/or port region with exterior dimensions which do not correspond with the interior configuration of the cap housing 110. The example of an embodiment of an adapter 130 illustrated in FIG. 7 has one or more hooks 132 along an upper surface thereof. As illustrated in FIG. 4 (and as may also be seen in FIGS. 2 and 3), the hooks 132 are configured to engage with the stabilizing tabs 118 of the cap housing 110 to hold the adapter 130 in place with respect to the cap housing 110 within the interior 111 of the cap housing 110. It will be appreciated that the term "hooks" is to be understood as not limiting to a particular shape or configuration and may be alternately referenced herein as fingers, flanges, projections, shoulders, latches, elements, members, or the like, without intent to limit. A hook 132 may be provided to extend over the upper surface of the one or more stabilizing tabs 118, such as on opposite sides of the stabilizing tabs 118, as illustrated in FIG. 4. As may be appreciated with reference to FIG. 3, the hooks 132 may fit between an upper surface of the stabilizing tabs 118 and a lower surface of the base 140, further contributing to holding the adapter 130 in place with respect to the cap housing 110. Although only one half of the adapter 130 fitted within the cap housing 110 is illustrated in FIG. 4, the other half of the adapter 130 and cap housing 110 may have a similar interior configuration.

The adapter 130 may also include a plurality of projections 134 along the upper surface of the adapter 130, as illustrated in FIG. 7. When the adapter 130 is positioned in the cap housing 110, the projections 134 may extend on either side of the locking tabs 116 in the cap housing 110 to hold the locking tabs 116 in place with respect to the port 1010, as may be appreciated with reference to FIG. 4. As such, the projections 134 may inhibit or prevent lateral shifting of the cap assembly 100 with respect to the port 1010. Although only one half of the adapter 130 fitted within the cap housing 110 is illustrated in FIG. 4, the other half of the adapter 130 and cap housing 110 may have a similar interior configuration.

The exterior 133 of the adapter 130 preferably is sized, shaped, configured, and dimensioned to correspond with the size, shape, configuration, and dimensions of the interior 111 of the cap housing 110. As may be appreciated with reference to FIG. 6 and FIG. 7, the adapter 130 may include one or more ribs 135 and/or grooves 137 corresponding with the one or more ribs 115 and/or grooves 117 on the interior 111 of the cap housing 110. Engagement of the engagement of the ribs 115 of the cap housing 110 with the grooves 137 of the adapter 130 and/or engagement of the ribs 135 of the adapter 130 with the grooves 117 of the cap housing 110 further enhance stable engagement of the adapter 130 with respect to the cap housing 110, and thereby provide a stronger, more stable connection of the cap assembly 100 to the medical device 1000. Such engagement may be considered to provide a surface-to-surface contact (contact of extended surfaces) in contrast with point-to-point contact (contact of limited extents).

With an adapter 130 securely in place within the lower portion 114 of the cap housing 110, such as described above, a cap housing 110 may be securely mounted on a second port sized, shaped, configured, and dimensioned differently from a first port sized, shaped, configured, and dimensioned to correspond with the interior configuration of the cap housing 110. As such, a cap housing 110 may be securely coupled to at least two differently sized, shaped, configured, and dimensioned ports. For instance, the adapter 130 effectively reduces the inner diameter of the cap housing 110 to allow the cap housing 110 to securely fit on a second port region narrower than the first port region on which the interior 111 of the cap housing 110 is dimensioned to securely fit. The adapter 130 also effectively increases the height to which the locking tabs 116 may extend about a neck of a port. The cap housing 110 thus may securely fit about a first neck region around the neck of a first port and between the upper flange of the first port and its corresponding or associated port region, as well as about a second neck region about the neck of a second port and between the upper flange of the second port and its corresponding or associated port region, the second neck region being larger than the first neck region.

Figure 8:
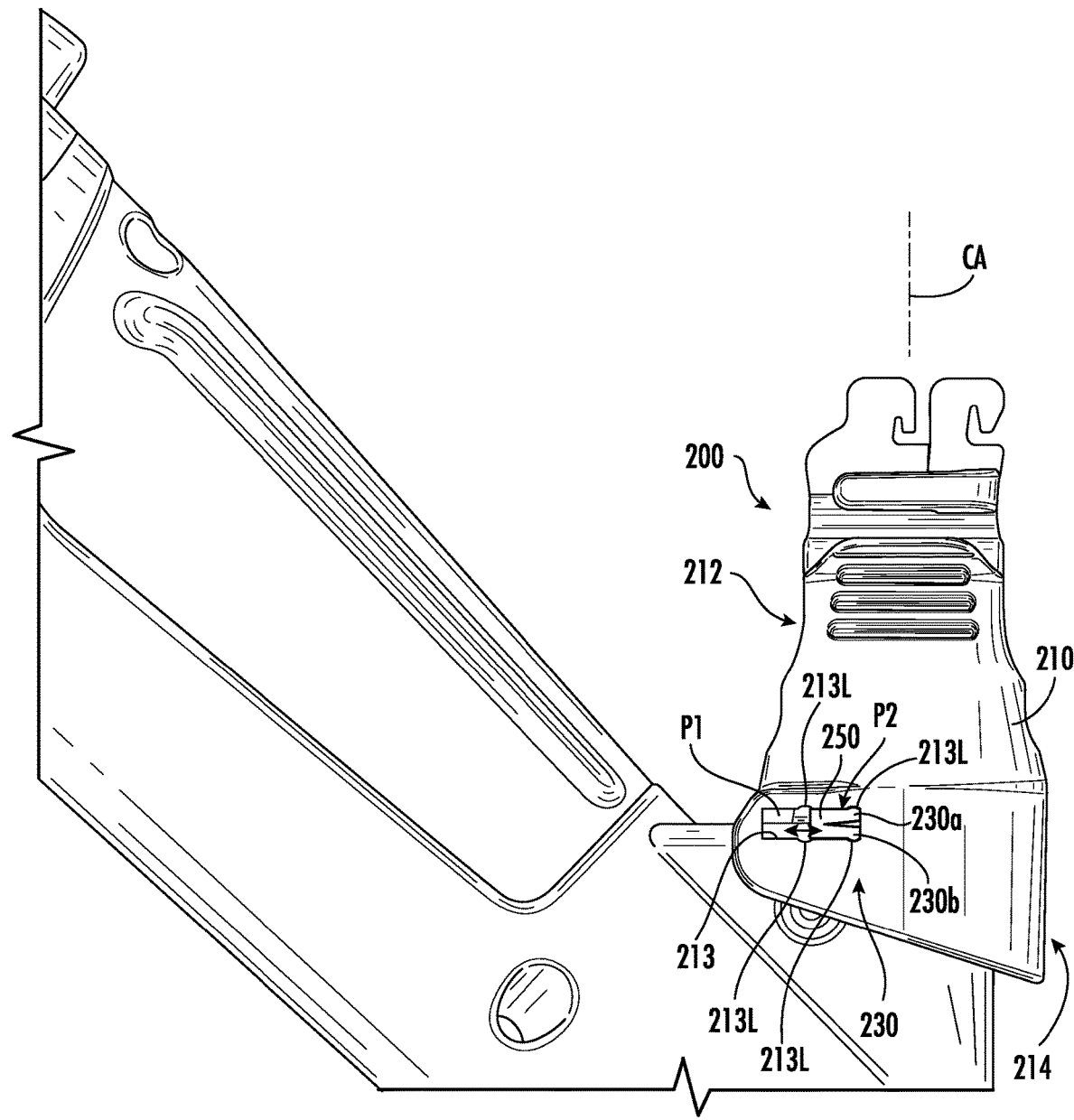
FIG. 8 is a side elevational view of another example of an embodiment of a cap assembly formed in accordance with various principles of the present disclosure.

In accordance with various principles of the present disclosure, another embodiment of a cap assembly 200, as illustrated in FIG. 8, may include an adapter 230 capable of shifting between at least two configurations to allow the cap assembly 200 to securely engage at least two ports of different sizes, shapes, configurations, and/or dimensions. The cap assembly 200 of FIG. 8 is illustrated in position with respect to a medical device 1000 similar to the medical device 1000 illustrated in FIG. 1. As with the cap housing 110 of the embodiment of FIG. 1, the cap housing 210 of the embodiment of FIG. 8 has an upper portion 212 in which a cap (such as the cap 120 illustrated in FIG. 1) may be positioned. Also as with the cap housing 110 of the embodiment of FIG. 1, the cap housing 210 of the embodiment of FIG. 8 has a lower portion 214 configured to engage a portion of the medical device 1000 such as surrounding a port 1010. The cap housing 210 may be formed from two mating cap housing halves 210a, 210b, as illustrated, for example, in FIGS. 9 and 11, to facilitate manufacturability and assembly of the cap assembly 200. The cap housing halves 210a, 210b may be coupled together in any known or heretofore known manner (such as with mating locking tabs 219 as illustrated), the details of which may be readily appreciated by one of ordinary skill in the art (such as with reference to the above-incorporated U.S. Patent Application Publication 2020/0138272) and are not provided herein as not necessary for an understanding of the principles disclosed herein with respect to cap assemblies, or caps, or cap housing, or adapters. As may be appreciated with reference to FIGS. 9, 10, and 12, the interior of the cap housing 210 may include stabilizing tabs 218. A base 140 of a cap 120 as illustrated in FIGS. 1-3 may be seated and stabilized on the stabilizing tabs 218. The adapter 230 may be securely fitted at a position within the cap housing 210 corresponding to the position of the locking tabs 116 of the cap housing 110 of FIGS. 1-7. For reasons as will become apparent, locking tabs 116 such as provided in the cap housing 110 of FIGS. 1-7 need not be provided in the cap housing 110 of FIGS. 8-13.

In the example of an embodiment illustrated in FIG. 8, an adapter actuator 250 extends through a window 213 in the lower portion 214 of the cap housing 210 to be accessible from an exterior of the cap housing 210. As may be appreciated with reference to FIGS. 9-13, one or more adapter actuators 250 (with respective windows 213) may be provided, one on each side of the cap housing 110. For the sake of simplicity, reference is made to components associated with one adapter actuator 250, it being appreciated that similar descriptions may apply to components associated with another adapter actuator 250 which may be used with the adapter 230 of FIGS. 8-13. The adapter actuator 250 is positioned with respect to the cap housing 210 to be moved between a first position $P_1$ and a second position $P_2$ to shift the adapter 230 between the at least two adapter configurations. In the embodiment illustrated in FIGS. 8, 9, and 11, the adapter actuator 250 has first and second legs 252a, 252b which are biased away from each other to fit within a corresponding locking region 213L in the window 213. In some embodiments, the ends of the first and second legs 252a, 252b are enlarged to fit in correspondingly enlarged locking regions 213L in the window 213 (one or more locking regions 213L may be provided). When the ends of the first and second legs 252a, 252b are in a locking region 213L of the window 213 in the cap housing 210, the adapter actuator 250 is inhibited or prevented from moving out of its position with respect to the cap housing 210, thereby holding the adapter 230 securely with respect to the medical device 1000 (and port 1010) on which the adapter 230 and cap assembly 200 are mounted. The first and second legs 252a, 252b of the adapter actuator 250 may be squeezed together to release the adapter actuator 250 from one locking region 213L to shift the adapter actuator 250 to another position (such as into another locking region 213L) to shift or adjust the configuration of the adapter 230.

Figure 9:
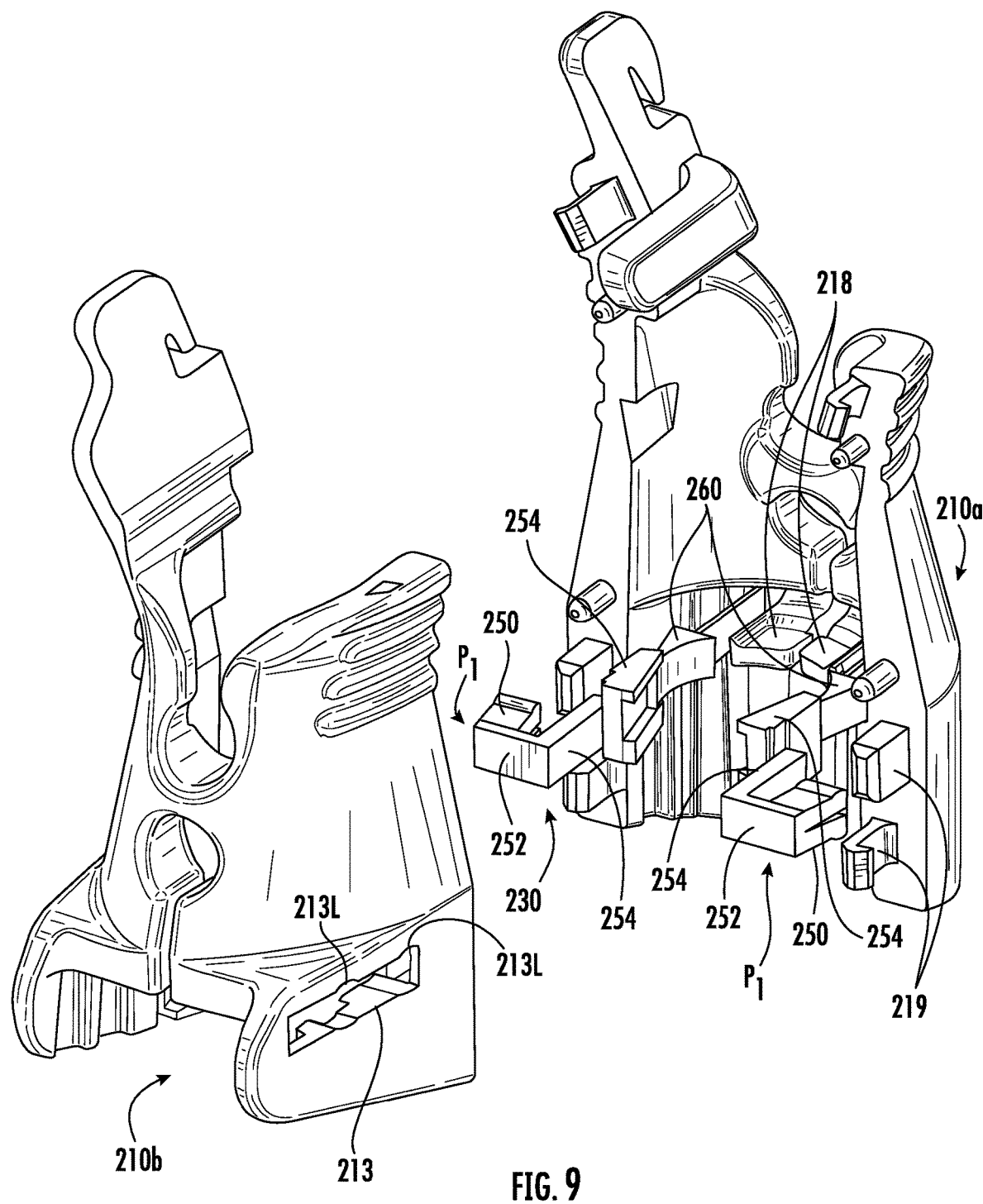
FIG. 9 is a perspective view of an example of a cap housing and adapter for a cap assembly such as illustrated in FIG. 8, with the halves of the cap housing shown in an exploded view and the adapter in a first configuration.
Figures 10, 12:
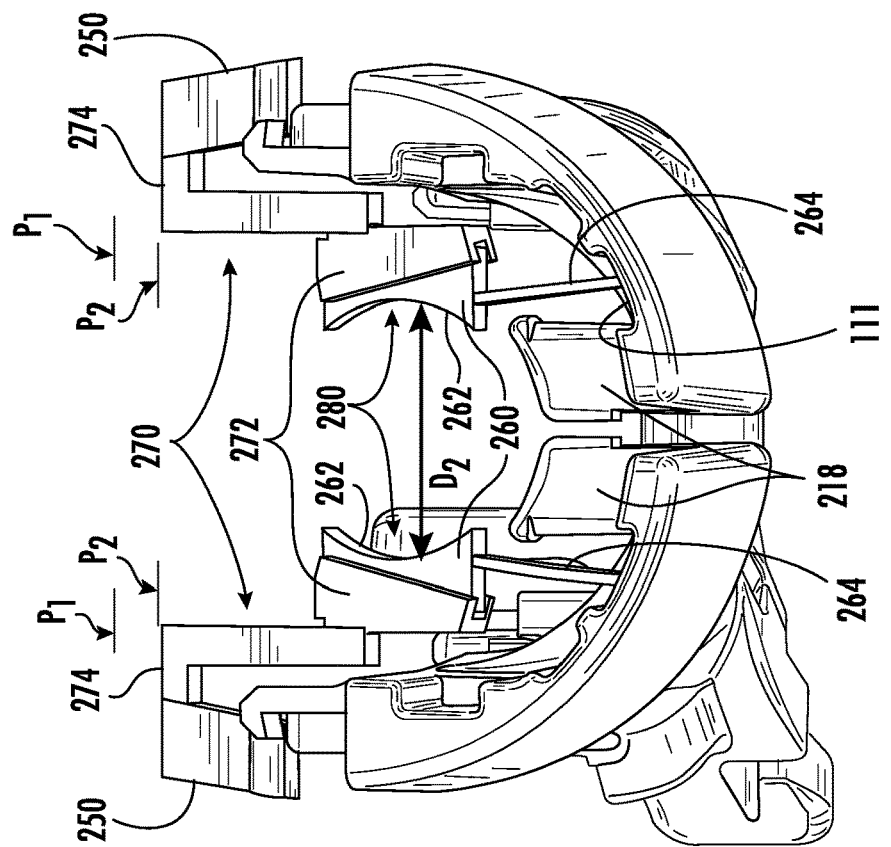
FIG. 10 is a bottom perspective view of an example of a half of a cap housing and adapter for a cap assembly such as illustrated in FIG. 9.
FIG. 12 is a bottom perspective view of an example of a half of a cap housing and adapter for a cap assembly such as illustrated in FIG. 11.
Figure 11:
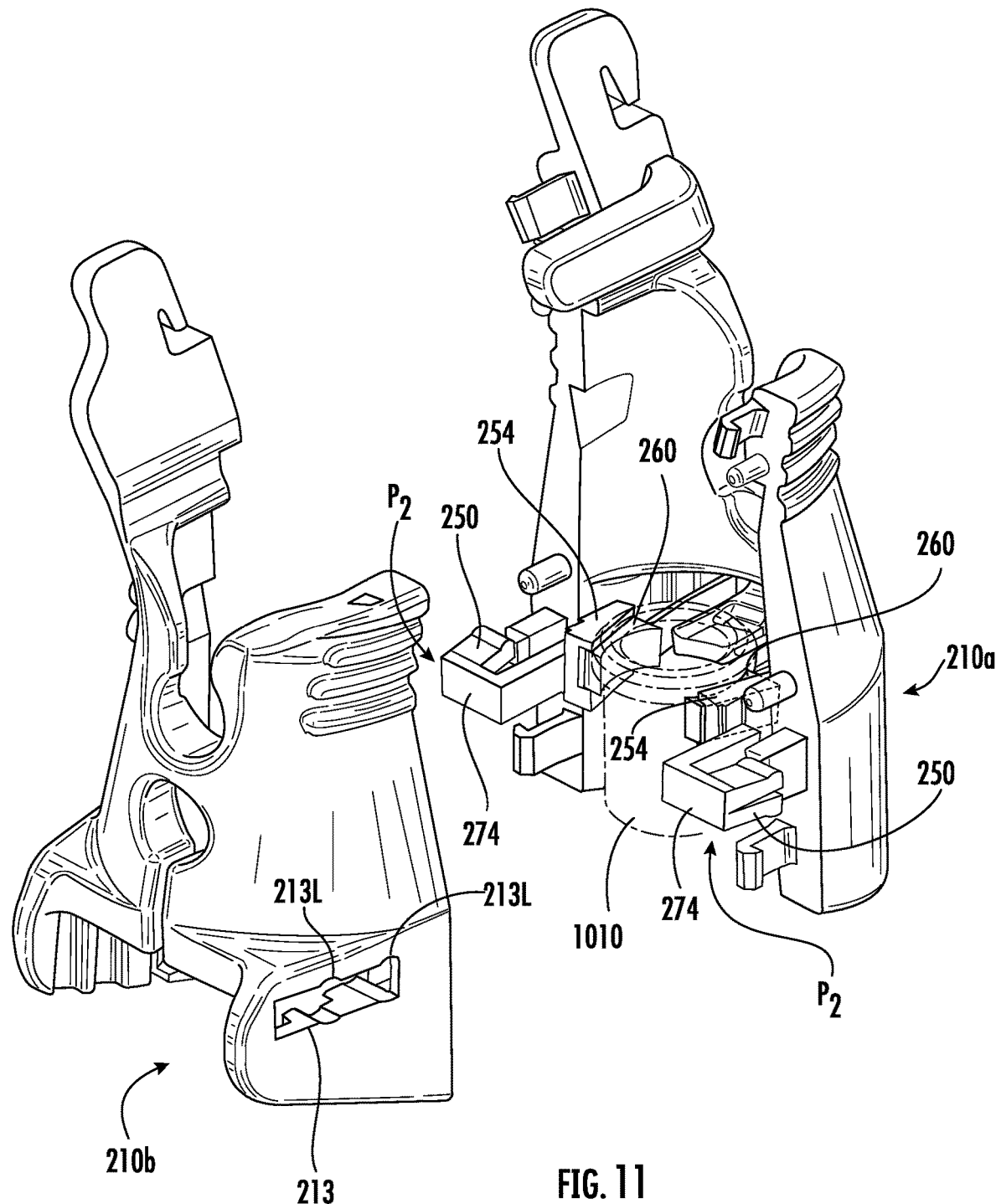
FIG. 11 is a perspective view of a cap housing and adapter as in FIG. 9, with the halves of the cap housing shown in an exploded view and the adapter in a second configuration.
Figure 13:
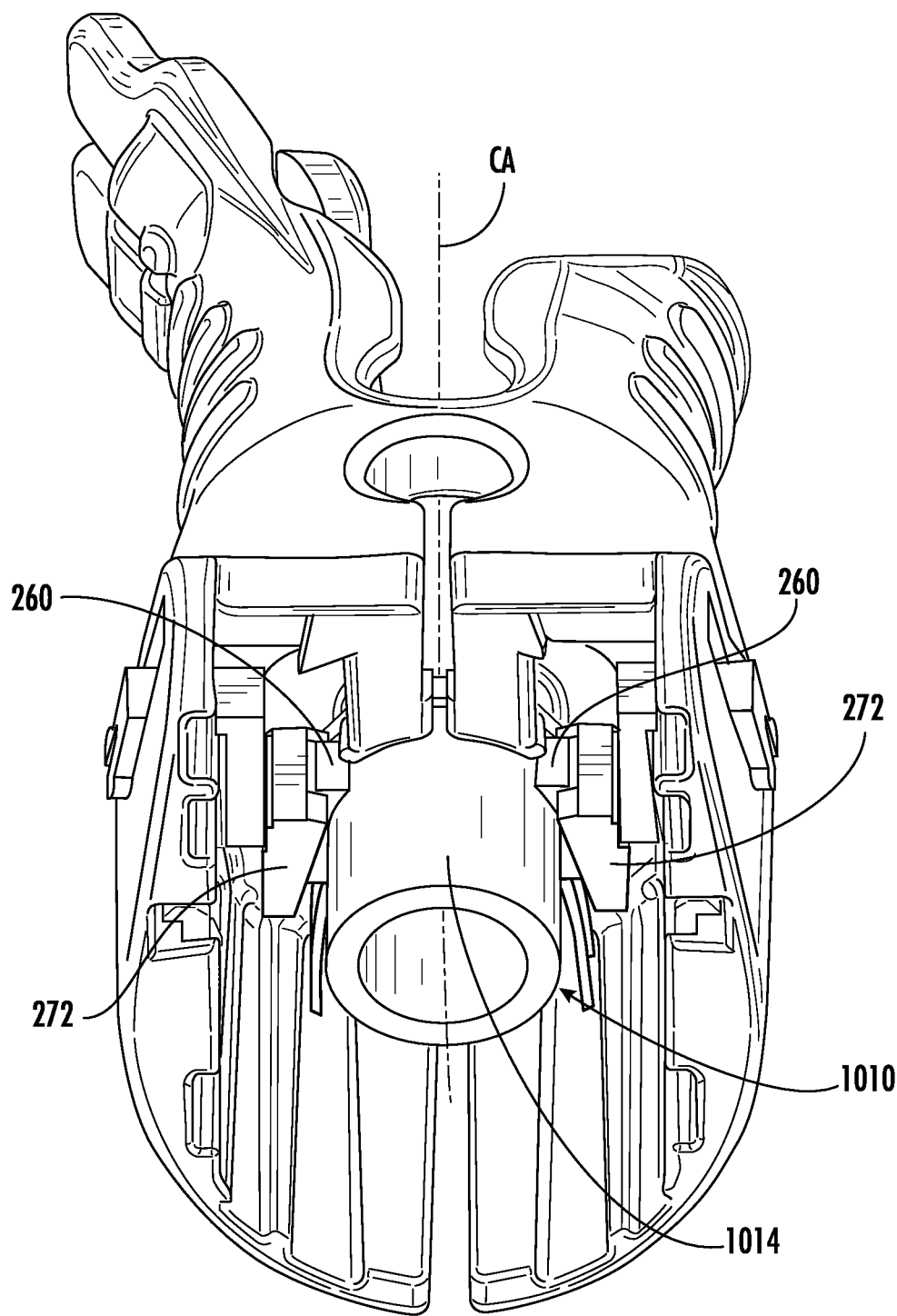
FIG. 13 is a bottom perspective view of an example of a cap housing and adapter such as in FIGS. 8-12, in a second configuration and illustrated as secured with respect to a neck of an example of a medical device port.

Referring to FIGS. 9-12, an embodiment of an adapter 230 formed in accordance with various principles of the present disclosure is illustrated as having at least two gripper portions 260 configured to grip against a port 1010 of a medical device 1000. For instance, the gripper portions 260 may include opposed gripper surfaces 262 which may be curved or otherwise shaped to correspond to the generally curved (or otherwise shaped or contoured) outer surfaces of the necks of medical device ports. The gripper portions 260 are shiftable by moving the adapter actuator 250 from the first position $P_1$ to the second position $P_2$. When the gripper portions 260 are in the first position, the adapter 230 is in the first adapter configuration, illustrated in FIGS. 9 and 10. When the gripper portions 260 are in the second position, the adapter 230 is in the second adapter configuration, illustrated in FIGS. 11 and 12. More particularly, when the adapter actuator 250 is in the first position $P_1$, the gripper portions 260 are in a first position a first distance $D_1$ away from each other, as illustrated in FIGS. 9 and 10. And, when the adapter actuator 250 is in the second position $P_2$, the gripper portions 260 are in a second position a second distance $D_2$ away from each other, as illustrated in FIGS. 11 and 12. The first distance $D_1$ and the second distance $D_2$ are measured from the same opposed points on the opposed gripper surfaces 262 of the gripper portions 260, and may, for instance correlate to the diameter of a neck of a medical device port which the gripper portions 260 are to grip. In other words, the opposed points may be on either end of a diameter of a neck of a medical device port gripped between the gripper surfaces 262. In the embodiment illustrated in FIGS. 9-12, the first distance $D_1$ is greater than the second distance $D_2$. As such, the adapter 230 grips around medical device ports with wider necks when in the first configuration than in the second configuration (in which the adapter 230 grips around ports with relatively narrower necks). The gripper portions 260 may be formed of a slip-resistant material so that secure gripping of the gripper portions 260 with respect to the neck of a medical device port inhibits or prevents movement of the cap assembly 200 relative to the port 1010 (e.g., along the central axis CA of the port 1010, as illustrated in FIGS. 8 and 13). Suitable materials include polymers such as elastomers or resins with a coefficient of friction relative to the material of the medical device port to resist slippage therebetween. One example of a suitable material is Delrin© acetyl resin sold by DuPont deNemours, Inc. Alternative materials include polyoxymethylenes (POM) such as Delrin® PC650 NC0010, HOSTAFORM MT® SlideX™ 1203, HOSTAFORM MT® SlideX™ 2404; acrylonitrile butadiene (ABS) materials such as Cycolac HMG47MD, Cycolac HMG94MD; acrylonitrile butadiene+ polycarbonate (ABS+PC) materials such as Cycoloy HC1204HF; PC materials such as Sabic Lexan HP4; polybutylene terephthalate (PBT) materials such as Sabic Valox HX215HP; or polyetherimide (PEI) materials such as Sabic Ultern HU1010.

In the example of an embodiment of a reconfigurable adapter 230 illustrated in FIGS. 9-12, the adapter 230 has at least one movable component 270 interacting with a gripper component 280 to shift the adapter 230 between the first and second configurations. The movable component 270 includes the above-described adapter actuator 250 (such as at one end of the movable component 270) and a cam actuator 272 coupled to the adapter actuators 250 such as via an L-shaped leg 274. The adapter actuator 250, the cam actuator 272, and the L-shaped leg 274 may be formed as a one-piece unit or from separate components coupled together. The gripper component 280 includes one of the above-described gripper portion 260, and mounting legs 264 mounting the gripper portion 260 to the interior 111 of the cap housing 110. The movable component 270 and/or the gripper component 280 (as a whole or portions thereof) can be either manufactured within the mold (e.g., of the cap housing 210) itself or can be UV glued after production of the cap housing 210, either of which providing sufficient strength. It will be appreciated that generally a gripper component 280 may be associated with each gripper portion 260 of the pair of gripper portions 260 described above, and a movable component 270 may be associated with each gripper component 280. However, one movable component 270 and one gripper component 280 are described herein, for the sake of simplicity and without intent to limit. As the movable component 270 moves with respect to the gripper component 280, the cam actuator 272 moves with respect to the gripper portion 260 to move the gripper portion 260 toward or away from an opposed gripper portions 260. In some embodiments, the cam actuator 272 and the gripper portion 260 may have corresponding cam surfaces 266, 276. Movement of a cam actuator 272 with respect to (e.g., towards or away from) a gripper portion 260 causes the respective cam surfaces 266, 276 to move or slide with respect to and along each other to cam the gripper portion 260 in the desired direction to achieve the desired adapter 230 configuration. Although a pair of movable components 270 and a pair of gripper components 280 are illustrated, it will be appreciated that a single movable component 270 may be provided to move a corresponding gripper portion 260 with respect to another gripper portion 260. The single movable component 270 may move one or more gripper components 280 to move one or more gripper portion 260 with respect to one or more gripper portion 280 which may not be moved by a corresponding movable component 270.

In use, the configuration of the adapter 230 of the embodiments of FIGS. 9-13 is readily adjusted by moving the adapter actuator 250 between a first position $P_1$ and a second position $P_2$. The adapter 230 is thereby readily shifted between a first configuration, in which the cap assembly 200 can be securely mounted over a first port of a medical device, and a second configuration, in which the cap assembly 200 can be securely mounted over a second port of a medical device. In the first configuration, the gripper portions 260 are spaced apart from each other a first distance (illustrated in FIGS. 9 and 10), and in the second configuration the gripper portions 260 are spaced apart from each other a second distance (illustrated in FIGS. 11 and 12), the first distance being greater than the second distance. Accordingly, the cap housing 210 of the embodiments illustrated in FIGS. 8-12 may be mounted securely on a first port having a neck with a first diameter, as well as on a second port having a neck with a second diameter smaller than the first diameter. Secure engagement of a cap housing 210 with an example of an adapter 230 as illustrated in FIGS. 9-13 is illustrated in FIG. 12 with respect to a port with a second, smaller diameter. As may be seen, the cam actuators 272 are engaged with the gripper portions 260 to hold the gripper portions 260 against the neck 1014 of a port 1010. It will be appreciated that the first port and the second port may be on the same medical device or on different medical devices.

As may be appreciated, a variety of components and structures may be provided on or in association with an adapter formed in accordance with various principles of the present disclosure to allow a cap assembly to have at least two different configurations corresponding to at least two different medical device ports. Accordingly, a cap assembly with desired characteristics need not be limited to use with only one specific port. As such, the present disclosure provides a cap device and associated systems and methods adaptable for use with more than one configuration of a port of a device such as an endoscope, and thus compatible with different ports and different devices. A common configuration of a device and system which provides sealable access to a working channel of a port may be readily modified for use with different ports of a device, or ports of different devices (from different manufacturers, or different sizes and/or types of devices from one or more manufacturers). The user of such adaptable device and system need not modify his or her methods of use or general familiarity with the device and system, as adaptability does not affect the form or function presented to the user. Moreover, a single type of device and system is compatible with and may be used across different devices (with minor modifications to adapt the device and system to the port with which the device and system are to be associated).

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. Reference signs in the claims are provided merely as a clarifying example and shall not be construed as limiting the scope of the claims in any way.

What is claimed is:

1. A cap assembly compatibly couplable to one or more medical devices, said cap assembly comprising:
   a housing having an upper portion configured to house a cap, a lower portion with an interior having a configuration corresponding with an exterior configuration of a first port of a medical device to securely engage the first port, and a radially-inwardly directed stabilizing shoulder extending inwardly from the interior of said lower portion of said housing between the upper portion and the lower portion; and
   an adapter securable within the interior of said housing and having an interior configuration corresponding with a second port having a different configuration from the first port to securely engage the second port, and a hook extending over a proximal, upper surface of said radially-inwardly directed stabilizing shoulder to hold said adapter in place with respect to said housing within the interior of the lower portion of the housing.

2. The cap assembly of claim 1, wherein said adapter has an exterior configuration corresponding to the housing lower portion interior configuration.

3. The cap assembly of claim 2, wherein the exterior of said adapter is engageable with the interior of said lower portion of said housing with a surface-to-surface contact.

4. The cap assembly of claim 3, wherein the housing lower portion interior includes one or more ribs or grooves and the adapter exterior includes one or more grooves or ribs mating with said housing ribs or grooves.

5. The cap assembly of claim 1, wherein:
   said cap assembly further includes a cap positioned within said housing upper portion; and
   said cap includes a base seated and stabilized on said stabilizing shoulder.

6. The cap assembly of claim 5, wherein said hook is fitted between an upper surface of said at least one stabilizing shoulder and a lower surface of said base.

7. The cap assembly of claim 1, wherein said housing includes a pair of locking tabs extending inwardly from opposite sides of the interior of said lower portion of said housing, said locking tabs being formed of a flexible, resilient, creep resistant, dimensionally stable material and configured to securely engage the first port or the second port.

8. The cap assembly of claim 7, wherein said adapter further comprises at least one projection positioned to engage one of said locking tabs to at least inhibit lateral shifting of said locking tabs with respect to the second port.

9. The cap assembly of claim 1, wherein the first port is on a first endoscope and the second port is on a second endoscope, said adapter configuring said housing for coupling to two different endoscopes.

10. An adapter for compatibly connecting a cap assembly with one or more different ports, said adapter comprising:
    an exterior configuration connectable to an interior of a cap housing having a distal end configured to securely engage an exterior of a first port of a medical device, the exterior configuration of said adapter including an exterior sized, shaped, configured, and dimensioned to correspond with the size, shape, configuration, and dimensions of the interior of the cap housing, and at least one hook positioned to extend over a proximal surface of a radially-inwardly extending shoulder in the interior of the cap housing; and
    an interior configuration sized, shaped, configured, and dimensioned to securely engage an exterior of a second port of a medical device having a different configuration from the exterior of the first port.

11. The adapter of claim 10, wherein:
    a portion of the cap housing interior has a configuration corresponding with a first port region of the medical device surrounding the first port to securely engage the cap assembly with the first port without said adapter fitted therein;
    said adapter exterior configuration establishes a surface-to-surface contact with the cap housing interior to securely fit within the cap housing; and
    said adapter interior configuration corresponds with the exterior configuration of a second port and a second port region surrounding the second port to securely engage the cap assembly, with said adapter fitted therein, with the second port, the second port region being different from the first port region.

12. An adapter configured to fit within the interior of a lower portion of a housing of a cap assembly to shift an interior configuration of the housing lower portion between a first configuration for securely engaging a first port of a medical device and a second configuration for securely engaging a second port of a medical device having a configuration different from the configuration of the first port, said adapter comprising:
    a gripper component comprising gripper portions with gripper surfaces shaped to securely engage a neck of a port of a medical device; and
    at least one movable component engaging one of said gripper portions within the housing lower portion;
    wherein:
    said at least one movable component is accessible from outside the housing to be movable with respect to said gripper component within the housing lower portion to move at least one of said gripper portions with respect to another gripper portion to change the interior configuration of the adapter between the first configuration and the second configuration; and
    said at least one movable component is shifted via an actuator accessible through a window in the housing lower portion.

13. The adapter of claim 12, wherein said at least one movable component moves more than one gripper portion.

14. The adapter of claim 12, wherein:
    said at least one movable component has a cam actuator with a cam surface;
    said at least one gripper portion has a cam surface corresponding with said cam actuator cam surface; and
    movement of said movable component with respect to said gripper component causes said cam actuator cam surface and said at least one gripper portion cam surface to slide with respect to each other to cause said at least one gripper portion to move with respect to another gripper portion.

15. The adapter of claim 12, wherein in the first configuration an interior configuration of said adapter corresponds with an exterior configuration of the first port, and in the second configuration the adapter interior configuration corresponds with an exterior configuration of the second port.

16. The adapter of claim 12, wherein said movable component is shifted to shift the relative positions of said gripper portions.

17. The adapter of claim 12, wherein:
said actuator is provided on said movable component;
said gripper component includes gripper portions with gripper surfaces shaped to correspond to the outer surfaces of a neck of either the first port or the second port; and
said movable component is movable to move said gripper portions between a first position at a first distance away from each other and a second position at a second distance away from each other, the first distance being greater than the second distance, to shift the configuration of said adapter between the first configuration and the second configuration.

18. The adapter of claim 12, wherein said movable component and said gripper component have corresponding cam surfaces.

* * * * *